United States Patent
McGuckin, Jr.

(10) Patent No.: US 8,695,605 B2
(45) Date of Patent: *Apr. 15, 2014

(54) FALLOPIAN TUBE OCCLUSION DEVICE

(75) Inventor: James F. McGuckin, Jr., Radnor, PA (US)

(73) Assignee: Rex Medical, L.P., Conshohocken, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/542,521

(22) Filed: Jul. 5, 2012

(65) Prior Publication Data

US 2012/0272970 A1 Nov. 1, 2012

Related U.S. Application Data

(63) Continuation of application No. 11/998,299, filed on Nov. 29, 2007, now Pat. No. 8,235,048.

(60) Provisional application No. 60/872,382, filed on Dec. 1, 2006.

(51) Int. Cl.
| | |
|---|---|
| A61F 6/06 | (2006.01) |
| A61B 17/00 | (2006.01) |
| A61D 1/06 | (2006.01) |
| A61M 31/00 | (2006.01) |
| A61F 2/06 | (2013.01) |

(52) U.S. Cl.
USPC ........... 128/831; 128/830; 128/887; 606/135; 604/515; 623/1.18; 623/1.2

(58) Field of Classification Search
USPC .......... 128/831, 830, 887, 842; 606/135, 193; 604/515, 517; 623/1.18, 1.2, 1.21, 1.37
See application file for complete search history.

(56) References Cited

U.S. PATENT DOCUMENTS

| | | | |
|---|---|---|---|
| 5,935,137 | A | 8/1999 | Sadaat et al. |
| 6,550,480 | B2 | 4/2003 | Feldman et al. |
| 6,705,323 | B1 | 3/2004 | Nikolchev et al. |
| 6,763,833 | B1 | 7/2004 | Khera et al. |
| 7,073,504 | B2 | 7/2006 | Callister et al. |
| 2002/0133223 | A1 | 9/2002 | Vito et al. |
| 2003/0015203 | A1 | 1/2003 | Makower et al. |
| 2005/0217680 | A1 | 10/2005 | Callister et al. |
| 2005/0274384 | A1 | 12/2005 | Tran et al. |

*Primary Examiner* — Victoria J Hicks
(74) *Attorney, Agent, or Firm* — Neil D. Gershon

(57) ABSTRACT

A device for occluding the fallopian tube including a wire composed of a shape memory material and an outer material encapsulating at least a portion of the wire. The device has a first elongated configuration for delivery and a second configuration for placement. In the second configuration, the wire moves toward its shape memory position and has a U-shape defined by a curved portion and first and second leg portions extending from the curved portion, the first and second leg portions extending downwardly from the curved portion and laterally outwardly.

9 Claims, 7 Drawing Sheets

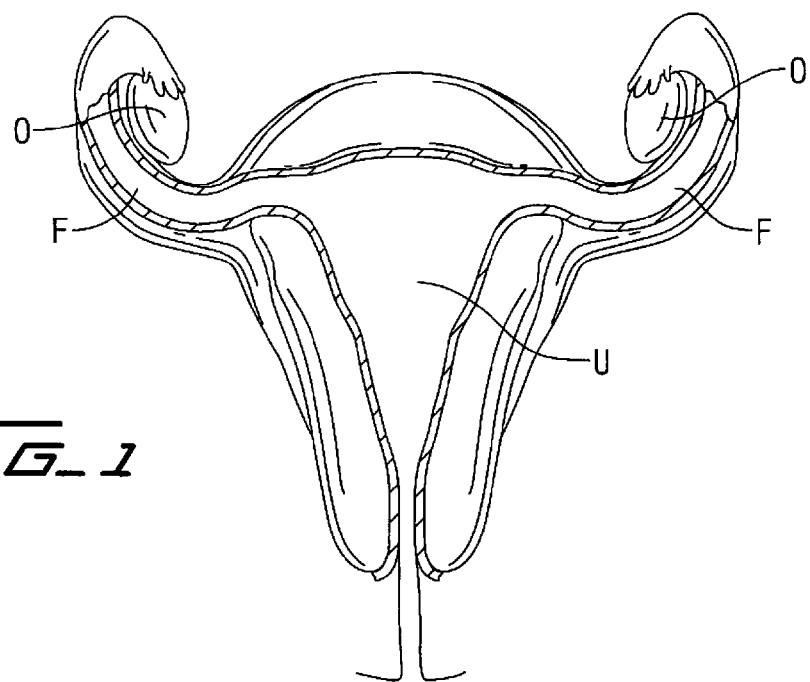
FIG_1
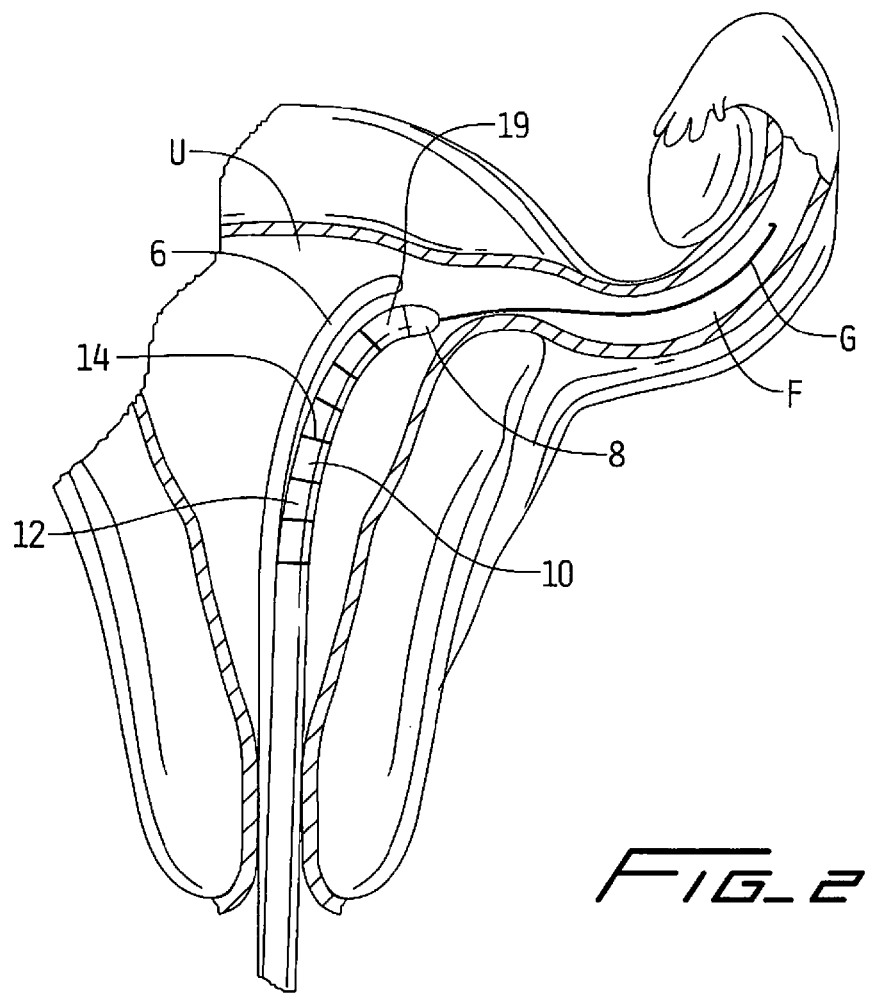
FIG_2

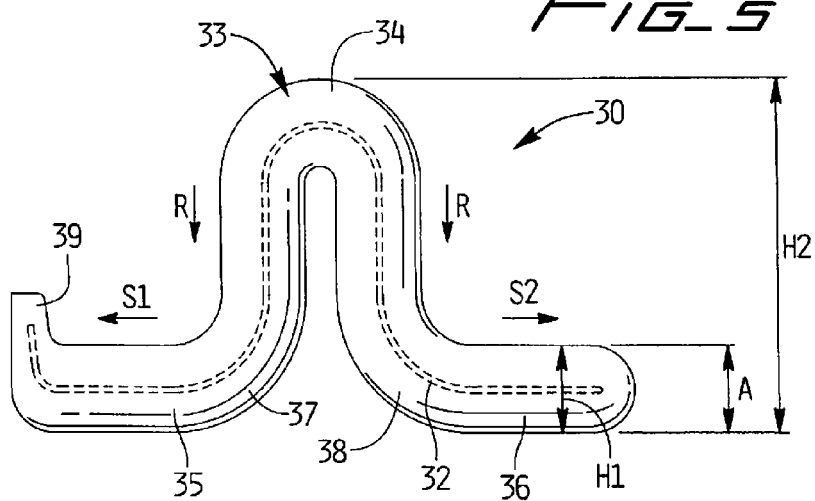
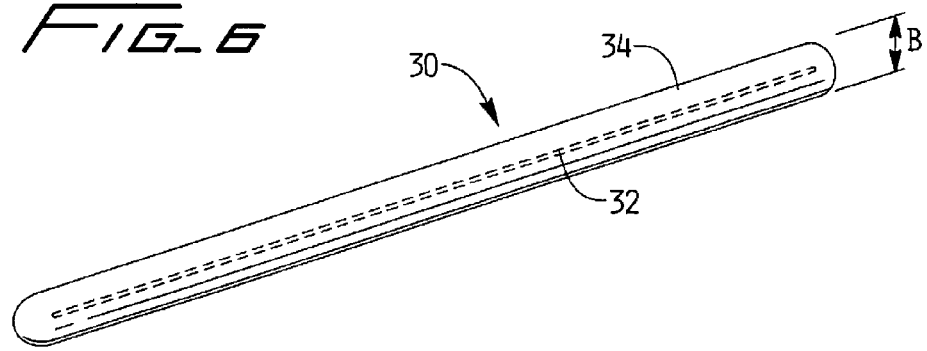
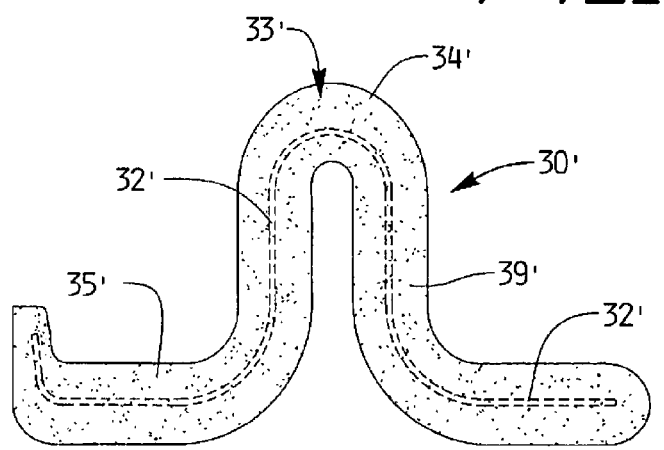

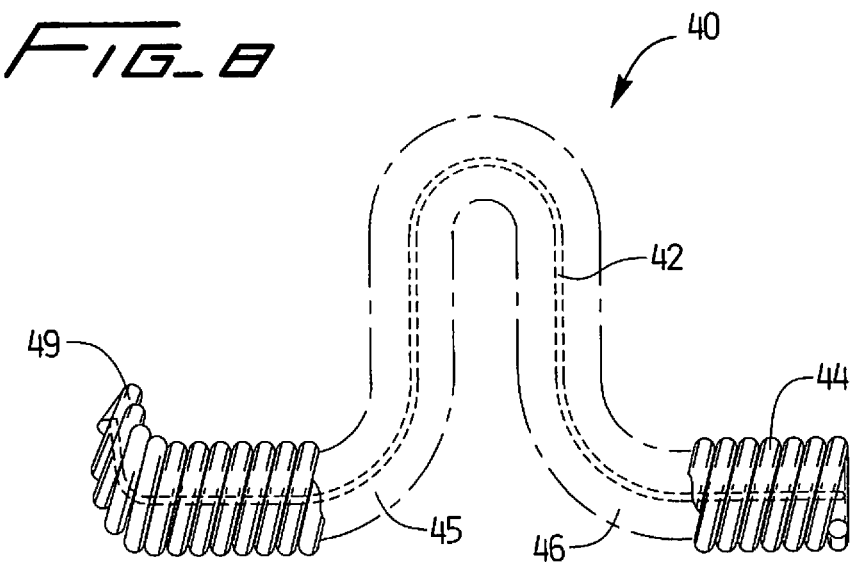
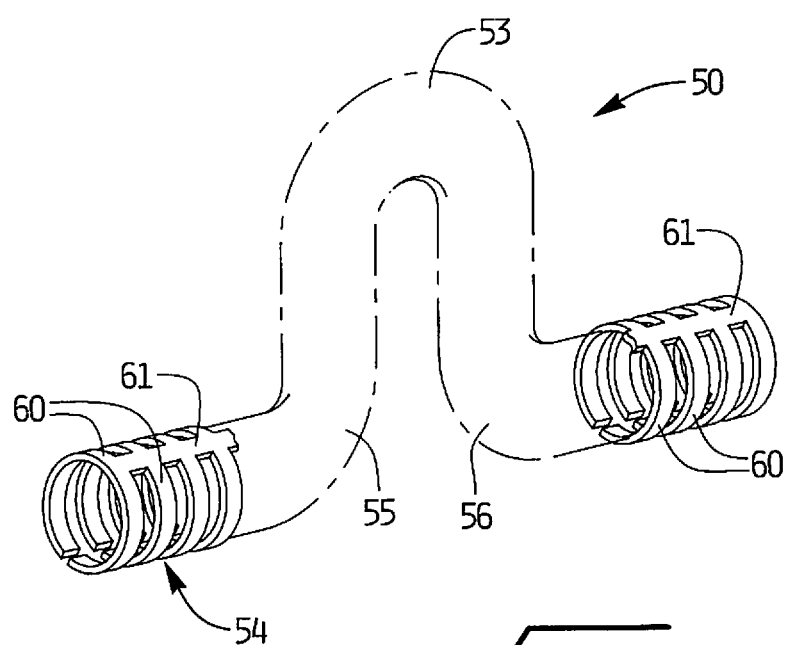

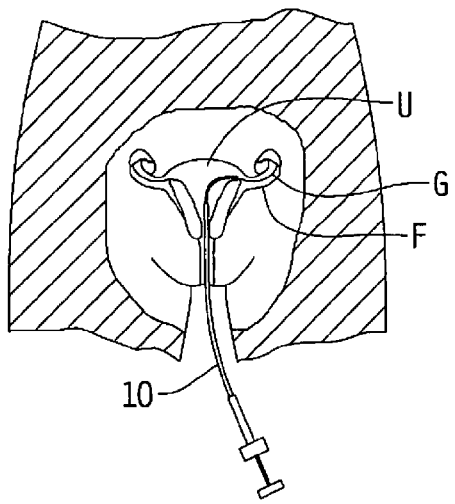
FIG_10
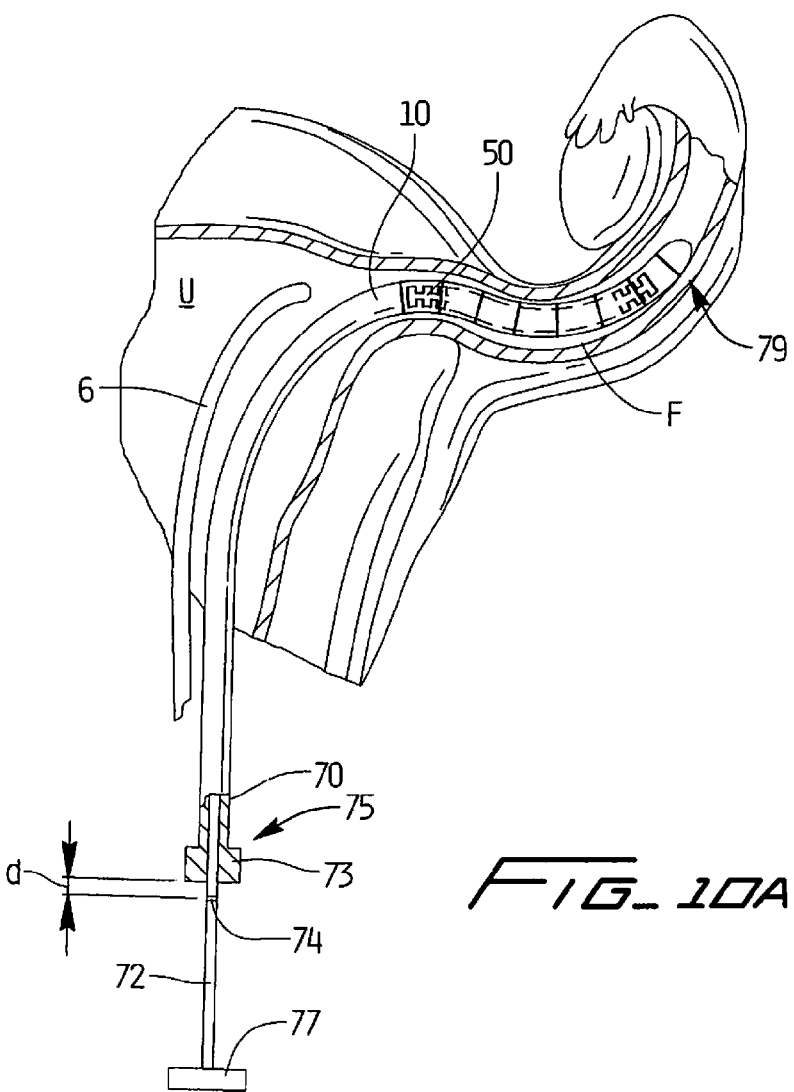
FIG_10A

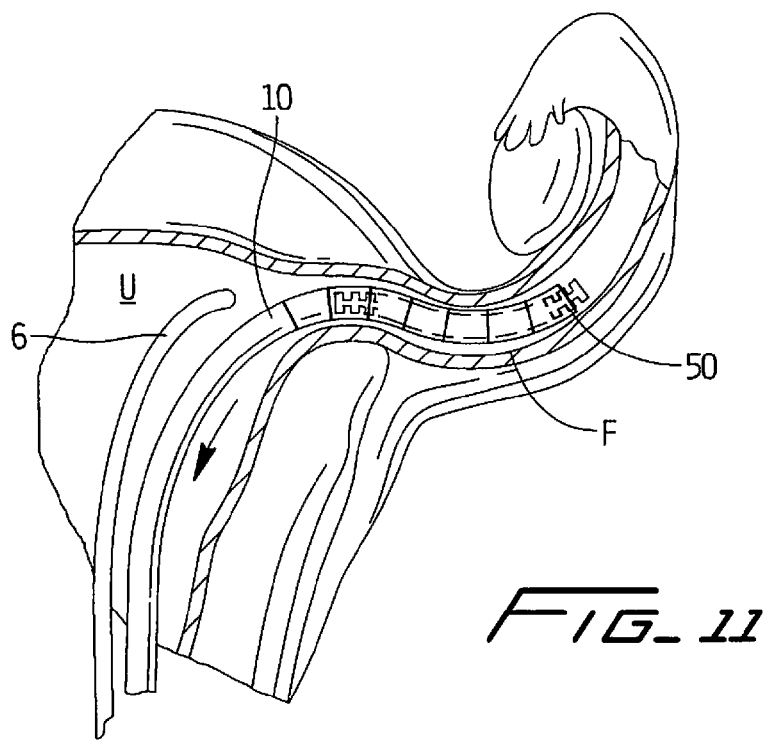
FIG_11
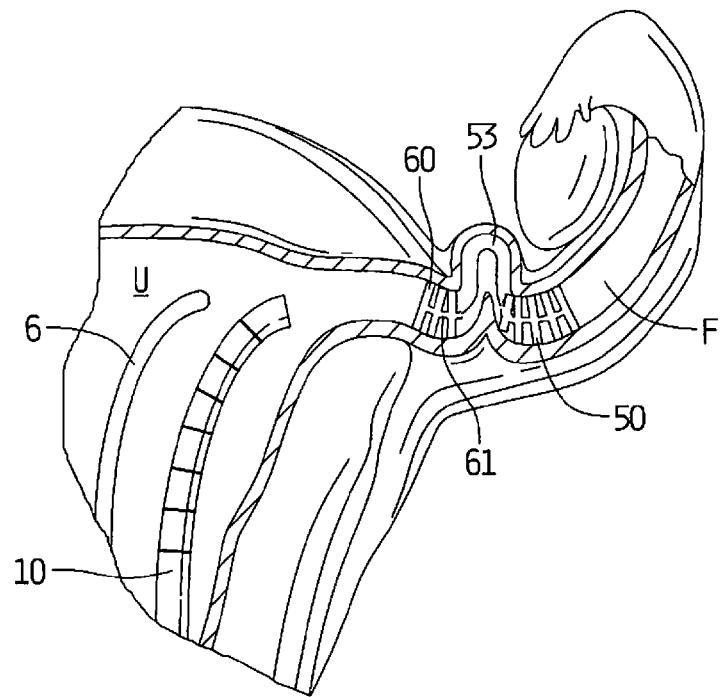
FIG_12

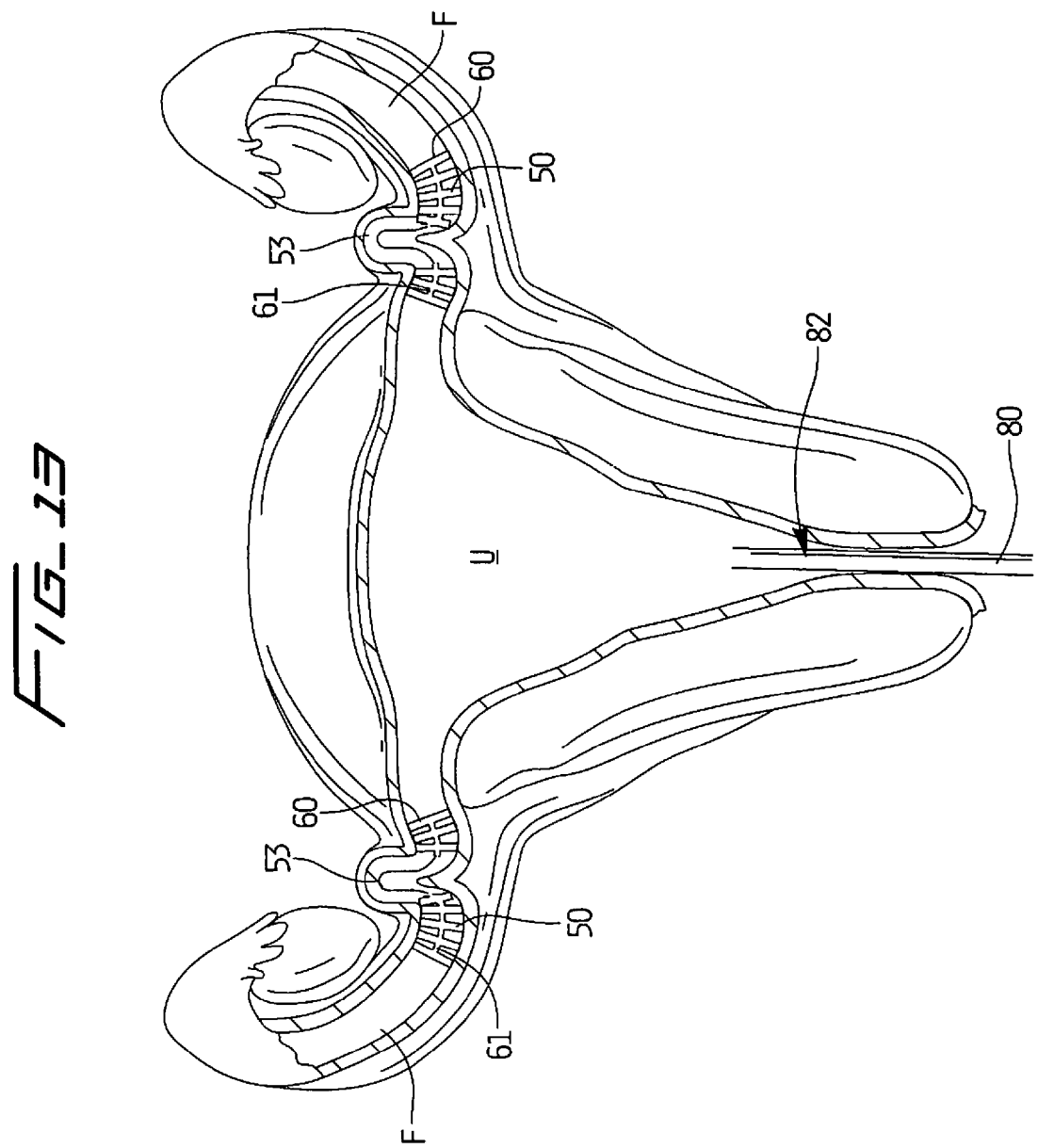

FALLOPIAN TUBE OCCLUSION DEVICE

This application is a continuation of application Ser. No. 11/998,299, filed on Nov. 29, 2007, which claims priority from provisional application Ser. No. 60/872,382, filed Dec. 1, 2006. The entire contents of each of these applications are incorporated herein by reference.

BACKGROUND

1. Field of the Invention

This application relates to a minimally invasive device for occluding the fallopian tubes.

2. Background of Related Art

Tubal ligation is one method of female sterilization. It can be performed laparascopically by access through the patient's abdomen where the surgeon severs and closes the ends of the fallopian tubes by tying, applying clamps or cauterization. These devices achieve occlusion by external application to the tube.

Other methods involve transcervical access. In some techniques, various agents are injected within each of the fallopian tubes to close or block the tubes. In other transcervical procedures, mechanical devices are inserted and anchored within the tube to promote tissue ingrowth and scar tissue formation to occlude the tubes. In other techniques, radiofrequency energy electrodes are inserted and energized to thermally damage the tube, causing scarring to occlude it.

The need exists for an improved device for occluding the fallopian tubes which can be inserted in a minimally invasive fashion.

SUMMARY

The present invention provides a device for occluding the fallopian tube comprising a wire composed of a shape memory material and an outer material encapsulating at least a portion of the wire. The device has a first elongated configuration for delivery and a second configuration for placement. In the second configuration, the wire moves toward its shape memory position and has a U-shape defined by a curved portion and first and second leg portions extending from the curved portion, the first and second leg portions extending downwardly from the curved portion and laterally outwardly.

In one embodiment, at least one of the legs has a hook extending upwardly toward the curved portion.

In one embodiment, a shape memory coil is positioned over the wire, and at least a portion of the coil is covered by the outer material.

The outer material can include a textured outer surface.

The implant preferably expands in a first orientation defined by movement from a straighter configuration to a U-shaped configuration and expands in a second orientation defined by movement from a first transverse dimension to a second larger transverse dimension.

In one embodiment, the implant is circular or oval in cross section such that in the second configuration a first diameter is less than a second diameter.

The present invention also provides a device for occluding the fallopian tube comprising a hypotube laser cut to form a series of ribs, the hypotube having a first elongated configuration for delivery and a second configuration for placement. In the second configuration, the hypotube has a substantially U-shaped portion with the curve of the U transitioning into first and second leg portions extending in a first direction, the first and second leg portions further extending outwardly in a second direction transverse to the first direction.

In one embodiment, the ribs are formed as a plurality of rings connected by a longitudinally extending spine wherein in the first configuration the rings have a first diameter and in the second placement configuration the rings have a second larger diameter.

A textured surface can be provided on the hypotube.

The present invention also provides a method for fallopian tube occlusion comprising the steps of:

inserting into the fallopian tube a first catheter having indicia to determine the depth of fallopian tube insertion;

inserting a second catheter through the first catheter, the second catheter having an implant positioned therein in an elongated configuration;

exposing the implant from the second catheter to enable it to expand to a U-shape configuration to thereby move a portion of the fallopian tube into a U-shape; and withdrawing the first and second catheters to leave the implant in the fallopian tube to fill the space within the tube to occlude the tube.

BRIEF DESCRIPTION OF THE DRAWINGS

Preferred embodiment(s) of the present disclosure are described herein with reference to the drawings wherein:

FIG. 1 is an anatomical drawing of the uterus and fallopian tubes;

FIG. 2 illustrates initial insertion of the delivery catheter and dilator over a guide wire under hysteroscope visualization;

FIG. 5 is a side view illustrating a first embodiment of the occlusion device in the unrestrained configuration (position);

FIG. 6 is a perspective view illustrating the occlusion device of FIG. 5 in the restrained configuration (position) where it is compressed and elongated;

FIG. 7 is a side view of an alternate embodiment of an occlusion device of the present invention having a textured surface;

FIG. 8 is a side view of another alternate embodiment of the occlusion device having a shape memory coil;

FIG. 9 is a perspective view of yet another alternate embodiment of the occlusion device formed of a hypotube laser cut to form ribs;

FIG. 10 is an anatomotical view illustrating placement of the delivery catheter in the fallopian tube and insertion of the delivery tube (sheath) containing the implant through the delivery catheter, the pusher shown in the retracted position;

FIG. 10A illustrates the delivery tube advancement into the fallopian tube;

FIG. 11 illustrates the direction of withdrawal of the delivery catheter;

FIG. 12 illustrates the delivery catheter and delivery tube withdrawn to expose the occlusion device to enable it to expand to its unrestrained locking shape; and FIG. 13 illustrates the occlusion device of the present invention placed in both fallopian tubes, and further showing a catheter inserted in the uterus to confirm the absence of leakage.

DETAILED DESCRIPTION OF PREFERRED EMBODIMENTS

Figure 3:
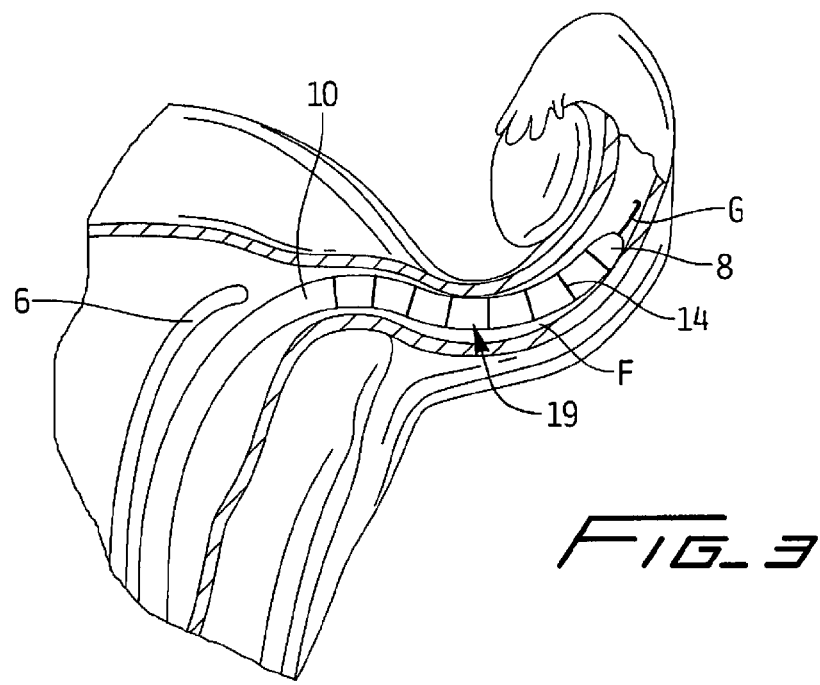
FIG. 3 illustrates further insertion of the delivery catheter into the fallopian tube, the catheter having a gauge to indicate the depth of penetration into the fallopian tube.

Referring now in detail to the drawings where like reference numerals identify similar or like components throughout the several views, an occlusion device for placement in the fallopian tubes for contraception is disclosed. The device provides a permanent, non-flouroscopic guided direct visualization system which can be inserted minimally invasively and preferably in an office procedure. A hysteroscope is used for direct visualization.

FIG. 1 is an anatomical drawing showing the vagina, cervix, uterus U, fallopian tubes F and ovary O. In FIG. 2, a delivery catheter 10, preferably having a curved distal end portion 19 as shown, is inserted into the uterus. A dilator 8 is positioned within the catheter 10, and the dilator 8 and catheter 10 are inserted over guidewire G, shown extending into the fallopian tube. Insertion over the wire provides longitudinal direction control as well as torqueability.

A series of gradations 14, for example numbers 1-7, although other markings are also contemplated, are provided on the outer surface 12 of catheter 10. The gradations could be radiopaque. The markings aid the physician in gauging how deep the delivery catheter 10 is placed into the fallopian tube for subsequent placement of the implant. A hysteroscope 6, also inserted through the vagina, provides for visualization of the markings.

FIG. 3 shows the catheter 10 positioned within the fallopian tube F, the markings providing a depth indicator within the fallopian tube as mentioned above. The dilator 8 protrudes past the distalmost end of catheter 10 to aid insertion of the catheter.

Figure 4:
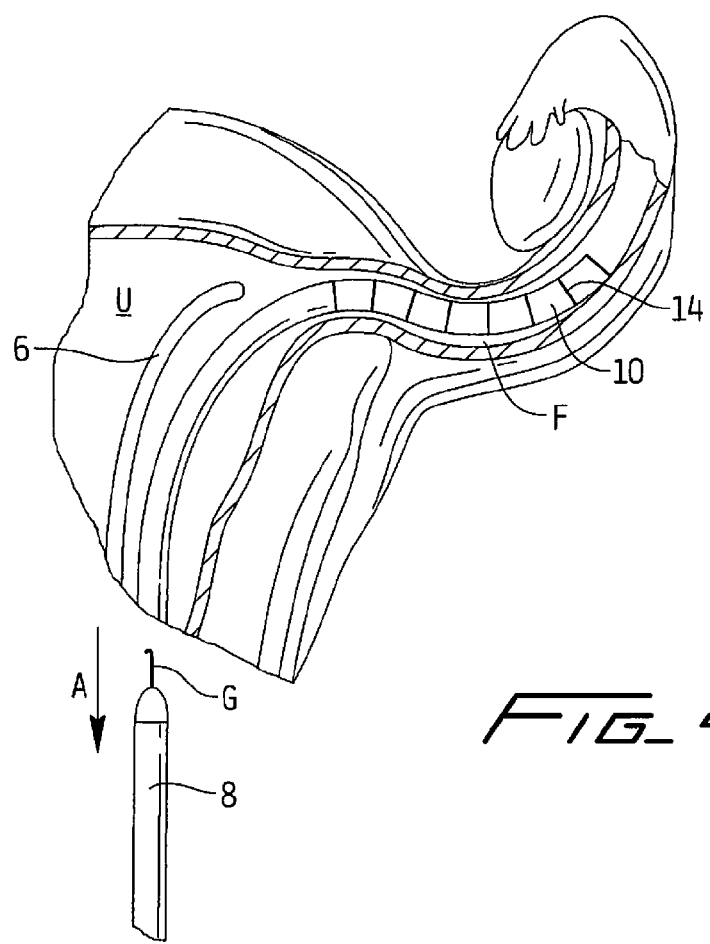
FIG. 4 illustrates the delivery catheter in position in the fallopian tube after removal of the dilator and guidewire.

The next step of the method is shown in FIG. 4, wherein the dilator 8 and guidewire G are withdrawn, in the direction of arrow A, after the scope 6 confirms the depth of penetration into the fallopian tube F. This leaves the catheter 10 in place at the desired depth within the fallopian tube for subsequent insertion of the implant which will be described in conjunction with the further method steps discussed below.

Turning now to the implant of the present invention, the implant is an occlusion device designed to occlude the lower end of the fallopian tube, i.e. by occupying the space and being non-porous, and designed to be self-expanding and self-retaining within the tube. Several embodiments of the implant are disclosed.

In a first embodiment illustrated in FIGS. 5 and 6, the implant (occlusion device) 30 comprises an interior portion in the form of wire 32 (shown in phantom) of self-expanding shape memory material, such as Nitinol. Other shape memory materials are also contemplated. The interior portion could be in forms other than a wire, such as a tube. The wire 32 is covered with PET, PTFE or other material 34 to encapsulate the wire 32. Although the entire wire 32 is shown encapsulated, it is also contemplated that not all of the wire is covered, provided a sufficient amount is covered so the device 30 can perform its function. The shape memory wire 32 provides the backbone or "spine" for maintaining the implanted shape of the occlusion device 30 as shown in FIG. 5.

In its restrained shape for delivery, as shown in FIG. 6, the implant 30 is compressed and elongated in a substantially cylindrical form, thereby allowing for minimally invasive delivery to the surgical site. In its unconstrained configuration, shown in FIG. 5, it has a curved portion 33 which extends in a U-shape, providing a locking contour to help retain the implant 30 in the fallopian tube.

The two legs (or leg portions) 35, 36 extend downwardly (as viewed in the orientation of FIG. 5), in the direction of arrow R, from the two ends of the U-curve and then transition at curved regions 37, 38 to extend laterally outwardly in opposite directions, (see arrows S1 and S2). Thus, the lateral portion of the legs 35, 36 extend transversely to the downwardly extending portions. The legs 35, 36 preferably have round surfaces to provide a less traumatic surface. One (or both) of the legs, e.g. leg 35, preferably has a hook 39, extending upwardly toward the curve of the U, to increase retention of the implant 30. In a preferred embodiment, the implant's self expansion is both in an upward direction (as viewed in FIG. 5) and in a lateral (radial) direction to fill the fallopian tube space, as indicated by the arrows in FIG. 7, which is also applicable to FIGS. 5, 8 and 9. That is, preferably the transverse dimension (or diameter) A (FIG. 5) of implant 30 in the expanded configuration exceeds the transverse dimension (or diameter) B (FIG. 6) of implant 30 in the more linear delivery position. This can be achieved by utilizing a shape memory material, in the form of a rod for example, that has a shape memorized position that is pre-set to the aforedescribed U-shape as well as pre-set to a larger diameter. When constrained for delivery, it would have a more linear configuration and a compressed configuration having a thinner configuration (smaller diameter/smaller transverse dimension). Release from the delivery tube or a change of temperature would transform it to the shape memorized position.

In the alternate embodiment of FIG. 7, implant (occlusion device) 30' has a outer material 34' with a textured surface 39' to promote friction to aid in self-retention. In all other respects, the implant 30' is identical to the implant 30 of FIG. 5, and designated with corresponding prime numerals. Such textured surface could be provided in the other implant embodiments disclosed herein. The implant 30' is shown in the expanded placement configuration with shape memory wire 32' in its shape memorized position.

The implant could also include a shape memory coil 44 placed over the shape memory wire 42 as shown in the embodiment of the implant 40 of FIG. 8. For clarity, only a portion of the coil 44 is shown, it being understood that the coil can extend over the entire wire 42 or only over a portion. In all other respects, the implant (occlusion device) 40 is identical to implant 30, e.g. curved portion 43, legs (leg portions) 45, 46, retention hook 49, etc.

In the alternate embodiment of FIG. 9, implant (occlusion device) 50 is formed from a hypotube 52 laser cut to form a series of ribs 54 forming a spine to give it its shape, with the ribs providing its self-expanding nature. As shown, the ribs include a series of rings 60, extending for almost 360 degrees, connected by a longitudinal spine 61. A membrane covering the hypotube could be provided. For clarity, only a portion of the ribs is shown, it being understood that the ribs extend over the entire region. In all other respects the implant 50 is identical to implant 30, e.g. curved portion 53, legs 55, 56, etc. A retention hook can be provided on one of the legs. Although the longitudinal spine is shown extending through the same region of the rings, it is also contemplated that the tube is cut such that the spine 61 is staggered (offset) so it joins different portions in the row of rings.

The implant 50 would be restrained in a compressed and substantially linear configuration for delivery, similar to the delivery shape of implant 30 shown in FIG. 6. When released from the delivery tube, it would self expand to the curved configuration of FIG. 9. It would also radially expand to the position of FIG. 9. That is, the diameter of the rings 60 would increase from a compressed smaller delivery diameter to a larger placement diameter. Thus, the ribs provide for expansion in different orientations.

Returning to the method of implant insertion, the implant of FIG. 9 is shown by way of example, but it should be appreciated that any of the other implants disclosed herein would be inserted in a similar manner. After withdrawal of the dilator 8 and guidewire G as explained above with respect to FIG. 4, the implant 50, which is contained within a delivery tube or sheath 70, is inserted through the catheter 10 as shown in FIGS. 10 and 10A. A pusher 72 with handle 77 extends from the proximal end 75 of delivery tube 70 and is configured to advance the implant within tube 70 to its distal end 79. Pusher 72 is shown in FIG. 10 in its retracted position. A marker 74 can be provided on the pusher 72 to provide a visual indicator when the pusher 72 has been advanced distally to a position corresponding to the positioning of the implant 50 at the distal end 79 of the delivery tube 70. That is, once the user sees the alignment of the marker 74 just proximal of the hub 73, indicated by a distance "d", the user knows the implant 50 is in the desired region of the fallopian tube.

The user than retracts the delivery catheter 10 and the delivery tube 70 in the direction of the arrow of FIG. 11 to expose the implant 50 from the catheter 10 as shown in FIG. 12. Note the hysteroscope 6 confirms the marker location on the delivery catheter 10 prior to uncovering the implant 50 to ensure it is properly delivered within the fallopian tube F. Once no longer restrained, the implant 50 returns to its shape memorized U-shaped expanded locking placement position (configuration) wherein it expands to a dimension to fill the fallopian tube as it deforms the fallopian tube to this shape. The U-shape aids the retention within the tube. The hook described above, if provided, engages the fallopian tube wall to also enhance retention.

A second implant, using the delivery catheter 10 and delivery tube 70 with pusher 72, is placed in the other fallopian tube in an identical manner. Either a separate delivery tube 70 and pusher 72 can be provided with an implant already loaded therein, or the same delivery tube and pusher from the first implant can be utilized by loading the second implant in the distal end of the tube 70 with the pusher 72 in the retracted position. After placement in both fallopian tubes, a catheter 80 with a side hole 82 (FIG. 13) can be inserted into the uterus to confirm there is no leakage.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure.

What is claimed is:

1. A device for occluding a fallopian tube comprising an interior portion and an outer material encapsulating the interior portion, the interior portion and outer material implantable in the fallopian tube, the device having a first elongated configuration for delivery constrained within a delivery tube and a second configuration for placement within the fallopian tube to occlude the fallopian tube, the device in the second configuration defining a U-shaped configuration defining a U and first and second leg portions extending laterally therefrom, the device having a first longitudinal length in the first elongated configuration for delivery and a second longitudinal length in the second configuration, the second longitudinal length being less than the first longitudinal length, when released from the delivery tube, the interior portion adapted to move toward the second configuration wherein the interior portion expands within the outer material in a longitudinal direction and in a lateral direction transverse to a longitudinal axis of the device, the first leg portion having a first height in the first elongated configuration of the device and a second height in the second configuration of the device, the second height being greater than the first height.

2. The device of claim 1, wherein the first leg portion has a hook.

3. The device of claim 2, wherein the hook extends upwardly toward a curve of the U.

4. The device of claim 3, wherein the interior portion comprises a wire.

5. The device of claim 1, wherein the interior portion comprises a wire.

6. The device of claim 5, wherein the wire is composed of a shape memory material.

7. The device of claim 1, wherein the device is substantially circular in cross section.

8. The device of claim 7, wherein the first leg portion has a hook portion.

9. The device of claim 1, wherein the first and second leg portions have round surfaces.

* * * * *